(12) United States Patent
Akiyama et al.

(10) Patent No.: US 10,464,102 B2
(45) Date of Patent: Nov. 5, 2019

(54) ULTRASONIC DETECTION DEVICE AND ULTRASONIC DIAGNOSTIC DEVICE

(71) Applicant: CANON KABUSHIKI KAISHA, Tokyo (JP)

(72) Inventors: Takahiro Akiyama, Kawasaki (JP); Makoto Takagi, Yokohama (JP); Kazunari Fujii, Kawasaki (JP); Hidemasa Mizutani, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 264 days.

(21) Appl. No.: 14/943,597

(22) Filed: Nov. 17, 2015

(65) Prior Publication Data

US 2016/0077058 A1 Mar. 17, 2016

Related U.S. Application Data (63) Continuation of application No. 13/393,918, filed as application No. PCT/JP2010/069642 on Oct. 28, 2010.

(30) Foreign Application Priority Data

Nov. 6, 2009 (JP) ................. 2009-254752

(51) Int. Cl.
*B06B 1/00* (2006.01)
*B06B 1/02* (2006.01)
*G01N 29/24* (2006.01)

(52) U.S. Cl.
CPC ....... *B06B 1/0292* (2013.01); *G01N 29/2406* (2013.01); *G01N 29/2418* (2013.01); *G01N 2291/101* (2013.01)

(58) Field of Classification Search
CPC .......... B06B 1/00; B06B 3/02; G01N 29/2406
See application file for complete search history.

(56) References Cited

U.S. PATENT DOCUMENTS 5,911,694 A   6/1999  Ikeda et al.
6,430,109 B1  8/2002  Khuri-Yakub et al.
(Continued)

FOREIGN PATENT DOCUMENTS

CN   101238754 A   8/2008
CN   201192347 Y   2/2009
(Continued)

OTHER PUBLICATIONS

Japanese Office Action in corresponding application No. 2014-094905 dated May 7, 2015—7 pages with English translation.
(Continued)

*Primary Examiner* — Hovhannes Baghdasaryan
(74) *Attorney, Agent, or Firm* — Venable LLP (57) ABSTRACT

Provided is an ultrasonic detection device including: a capacitive electromechanical transducer including a cell that includes a first electrode and a second electrode disposed so as to oppose with a space; a voltage source for developing a potential difference between the first electrode and the second electrode; and an electric circuit for converting a current, which is caused by a change in electrostatic capacitance between the first electrode and the second electrode due to vibration of the second electrode, into a voltage, in which the capacitive electromechanical transducer provides an output current with a high-pass characteristic having a first cutoff frequency with respect to a frequency, the electric circuit provides an output with a low-pass characteristic having a second cutoff frequency with respect to the frequency, and the second cutoff frequency is smaller than the first cutoff frequency.

25 Claims, 5 Drawing Sheets

(56) References Cited

U.S. PATENT DOCUMENTS

| | | |
|---|---|---|
| 6,957,582 B1 | 10/2005 | Durkee |
| 7,339,384 B2 | 3/2008 | Peng et al. |
| 7,515,948 B1 | 4/2009 | Balberg et al. |
| 2004/0113524 A1 | 6/2004 | Baumgartner et al. |
| 2004/0178938 A1 | 9/2004 | Pedersen |
| 2005/0111683 A1 | 5/2005 | Chabries et al. |
| 2005/0119575 A1 | 6/2005 | Ladabaum et al. |
| 2005/0243322 A1 | 11/2005 | Lasker et al. |
| 2006/0079740 A1 | 4/2006 | Silver et al. |
| 2006/0253025 A1 | 11/2006 | Kaufman |
| 2006/0273805 A1 | 12/2006 | Peng et al. |
| 2007/0287912 A1 | 12/2007 | Khuri-Yakub et al. |
| 2009/0036761 A1 | 2/2009 | Abreu |
| 2009/0048522 A1 | 2/2009 | Huang |
| 2010/0271188 A1 | 10/2010 | Nysen |
| 2012/0163124 A1 | 6/2012 | Akiyama et al. |

FOREIGN PATENT DOCUMENTS

| | | | |
|---|---|---|---|
| CN | 101524682 A | 9/2009 | |
| JP | 1-262000 A | 10/1989 | |
| JP | 2011-098071 A | 5/2011 | |

OTHER PUBLICATIONS

Yaralioglu IEEE transactions on ultrasonics, ferroelectrics, and frequency control, vol. 52, No. 12, Dec. 2005, pp. 2185-2198.

I. O. Wygant et al., "Integration of 2D CMUT Arrays with Front-End Electronics for Volumetric Ultrasound Imaging", IEEE Transactions on Ultrasonics, Ferroelectrics, and Frequency Control, vol. 55, No. 1, pp. 327-342 (Feb. 2008).

Office Action issued in counterpart Chinese Patent Application No. 201410403551.2 dated Dec. 31, 2015 (19 pages).

ULTRASONIC DETECTION DEVICE AND ULTRASONIC DIAGNOSTIC DEVICE

The present application is a continuation of U.S. application Ser. No. 13/393,918, filed on Mar. 2, 2012, which is a national phase entry of PCT/JP2010/069642, filed on Oct. 28, 2010, which claims priority to JP 2009-254752, filed Nov. 6, 2009, the entire disclosure of each of which is incorporated by reference herein.

TECHNICAL FIELD

The present invention relates to an ultrasonic detection device and an ultrasonic diagnostic device, and more particularly, to a capacitive ultrasonic detection device and an ultrasonic diagnostic device using the same.

BACKGROUND ART

Up to now, a capacitive ultrasonic detection device which includes a cell having electrodes disposed at an interval has been known (refer to U.S. Pat. No. 6,430,109). In particular, in recent years, capacitive micro-machined ultrasonic transducers (CMUT) using a micromachining technology have been actively researched. The CMUT transmits or receives an ultrasonic wave by the aid of a lightweight vibrating membrane, and can easily obtain an excellent broadband characteristic even if the transducers are placed in liquid and gas. Attention has been increasingly paid to ultrasonic diagnosis using the CMUT, with higher precision than that in the related-art medical diagnosis modality as a hopeful technology. The ultrasonic receiving function of the CMUT is performed by a capacitive electromechanical transducer and an electric circuit disposed at a later stage. An output of the prestage capacitive electromechanical transducer is caused by a temporal variation of an electrostatic capacitance, and hence the output is a current output. Accordingly, it is general to use a current-voltage conversion and amplification circuit at a later stage.

On the other hand, up to now, a piezoelectric material has been mainly used for the practical ultrasonic transducer. The resolution of the piezoelectric type device is proportional to the frequency, and hence the ultrasonic transducer normally has the center sensitivity in a range of from 3 MHz to 10 MHz. As compared with the piezoelectric type device, the CMUT has a feature of a broad frequency band. However, the piezoelectric type is about to be replaced with the related-art general ultrasonic diagnosis sensor, and hence the center frequency of this sensor is also generally about 3 MHz to 10 MHz. However, in order to effectively use the broad frequency band, a broad band is also required for the later stage electric circuit. The frequency characteristic of the ultrasonic receiving function of the CMUT is generally configured as a band pass type between the cutoff frequency of the capacitance electromechanical transducer and the cutoff frequency of an amplifier circuit. Therefore, the amplifier circuit having the cutoff frequency sufficiently larger than the receive band is frequently used. Regarding this matter, "IEEE Translations on Ultrasonics, Ferroelectrics, and Frequency Control, Vol. 55, No. 2, February 2008" discloses an amplifier circuit having a feedback resistance and a feedback capacitance, which is a capacitance parasitically existing in a MOS transistor circuit. As a result, the frequency band of the CMUT disclosed in the above-mentioned publication falls within a range of from 2 MHz to 7 MHz.

SUMMARY OF INVENTION

Technical Problem

Under the above-mentioned technical circumstances, in a specimen test, the ultrasonic transducers, which display not only a configuration image but also a function image, have been increasingly developed in recent years. As one of the ultrasonic transducers of this type, there is an ultrasonic transducer using a photoacoustic spectrometry. A frequency band of a photoacoustic wave used in the photoacoustic spectrometry is generally low as compared with a frequency band of an ultrasonic wave used in an ultrasonic echo. For example, the frequency band of the photoacoustic wave is distributed in a range of from 200 KHz to 2 MHz, which is lower than a center frequency 3.5 MHz of the ultrasonic wave used in the ultrasonic echo. For that reason, an ultrasonic transducer that can detect a relatively low frequency band with a high sensitivity needs to be developed.

Solution to Problem

In view of the above-mentioned problem, an ultrasonic detection device according to the present invention includes a capacitive electromechanical transducer, a voltage source, and an electric circuit, and has the following features. The capacitive electromechanical transducer includes a cell including a first electrode and a second electrode disposed so as to oppose with a space. The voltage source is for developing a potential difference between the first electrode and the second electrode. The electric circuit is for converting a current, which is caused by a change in electrostatic capacitance between the first electrode and the second electrode due to vibration of the second electrode, into a voltage. The capacitive electromechanical transducer provides an output current with a high-pass characteristic having a first cutoff frequency with respect to a frequency, and the electric circuit provides an output with a low-pass characteristic having a second cutoff frequency with respect to the frequency. Further, the second cutoff frequency is smaller than the first cutoff frequency.

Further, in view of the above-mentioned problem, an ultrasonic diagnostic device according to the present invention includes the ultrasonic detection device described above, a light source, and a signal processing system that processes a signal detected by the ultrasonic detection device. Further, light emitted from the light source is applied to an object to be tested, an elastic wave generated by a photoacoustic effect due to the light applied to the object to be tested is detected by the ultrasonic detection device, and a detection result is processed by the signal processing system to acquire information on the object to be tested.

Advantageous Effects of Invention

According to the present invention, the cutoff frequency of the current-voltage conversion and amplification circuit is set to be larger than the cutoff frequency of the capacitive electromechanical transducer, and those frequency characteristics are conformed to each other for the purpose of providing the frequency characteristic of the ultrasonic detection device. Therefore, the ultrasonic detection device having a lower frequency band than that of the related-art ultrasonic probe as a band can be realized. Further, the ultrasonic diagnostic device suitable for the photoacoustic spectrometry can be provided by the ultrasonic detection device, the light source, and the signal processing system.

Further features of the present invention will become apparent from the following description of exemplary embodiments with reference to the attached drawings.

DESCRIPTION OF EMBODIMENTS

Hereinafter, an ultrasonic detection device and an ultrasonic diagnostic device according to embodiments of the present invention are described.

The significant feature of the devices according to the present invention resides in that a second cutoff frequency of a frequency characteristic of a low-pass characteristic of an output from an electric circuit is made smaller than a first cutoff frequency of a frequency characteristic of a high-pass characteristic of an output current from a capacitive electromechanical transducer. The definitions of those cutoff frequencies, the high-pass characteristic, and the low-pass characteristic are described. As described later, the frequency characteristic of the output from the capacitive electromechanical transducer is maximum at the resonance frequency of a vibrating membrane in a vacuum. That is, when the vibrating membrane vibrates at the resonance frequency, the maximum value of the output is obtained. The frequency characteristic of the present invention is the frequency characteristic of the band-pass characteristic between antiresonant frequencies through the resonance frequency from a frequency (first cutoff frequency) lowered by about 3 dB at a frequency side lower than the maximum frequency. In the device actually fabricated, an average value in a range close to the frequency of the maximum output can be used to define the first cutoff frequency. The frequency characteristic of a capacitive mechano-electrical transducer in this case is a high-pass characteristic having the first cutoff frequency. That is, the high-pass characteristic in the present invention has a distribution that has the gain increased at a substantially given slope with respect to the frequency in a frequency domain lower than the cutoff frequency, and is flat in a frequency domain higher than the cutoff frequency. On the other hand, the later stage current-voltage conversion and amplification circuit has the frequency characteristic of the low-pass characteristic having the second cutoff frequency determined according to the values of the feedback resistance and the feedback capacitance. The low-pass characteristic in the present invention has a distribution that has the gain decreased at a given slope with respect to the frequency in a frequency domain higher than the cutoff frequency, and is flat in a frequency domain lower than the cutoff frequency. In this case, the second cutoff frequency means a frequency indicative of the gain lowered from the gain in the low band by about 3 dB. Specifically, the low-pass characteristic becomes "flat" in a domain lower than the cutoff frequency, and has "the gain decreased at the given slope" in the domain higher than the cutoff frequency. Likewise, the high-pass characteristic has "the gain increased at the given slope" in the domain lower than the cutoff frequency, and becomes "flat" in the domain higher than the cutoff frequency. In the present invention, the "distribution that is flat" means the given gain, but includes not only a case where the distribution is completely flat, but also a case where the slope of the gain with respect to the frequency characteristic is as small as the slope which can be ignored in the device design.

Based on the above concept, the ultrasonic detection device and the ultrasonic diagnostic device according to the present invention have the basic configuration described above. Embodiments described below can be implemented based on the basic configuration. For example, the capacitive electromechanical transducer includes a first electrode arranged on a substrate, a second electrode facing the first electrode, an insulator and a space which are held between the first electrode and the second electrode, and a vibrating membrane that vertically vibratably supports the second electrode (refer to Embodiment 1 described later). Further, in the ultrasonic detection device, a capacitor including the first electrode and the second electrode includes multiple spaces and multiple second electrodes or vibrating membranes. The characteristic of the output current of the capacitive electromechanical transducer is determined according to factors including the average of the mechanical characteristics of the multiple second electrodes or vibrating membranes and the electrostatic capacitance of the capacitor (refer to Embodiment 2 described later). In the ultrasonic detection device, the capacitors are arranged two-dimensionally, and vibration information of the second electrodes or vibrating membranes can be detected two-dimensionally (refer to Embodiment 3 described later).

A principle of the present invention is described. In the capacitive electromechanical transducer, it is not easy to set the center frequency band to about 1 MHz from the viewpoint of design. This is because, in order to set the center frequency band to about 1 MHz, the hardness of the second electrode or the vibrating membrane, which is a membrane, needs to be softened (reduced in spring constant), and there is an adverse effect that the sensitivity is deteriorated with the softened membrane, with the result that the degree of freedom of design is limited. That is, the membrane deflection becomes large, thereby making it difficult to produce a narrow space structure for high sensitivity. Further, an applied voltage to the electrodes is required to be decreased, and therefore the sensitivity is lowered. Under the circumstances, the present invention provides a system in which, under a state in which the capacitive electromechanical transducer is designed to have the center frequency at the higher frequency side from about 1 MHz, the cutoff frequency of the later stage electric circuit is adjusted so that the center frequency band is about 1 MHz in total. In such an intended relatively low frequency band, the adjustment of the cutoff frequency of the electric circuit while keeping a high amplification gain to some degree is relatively easy with hardly adversely affecting the other characteristics. On the contrary, an increase in the cutoff frequency while keeping the high amplification gain of the electric circuit is equivalent to a reduction in the feedback resistance or a reduction in the feedback capacitance. This causes the deterioration of the S/N ratio, or the deterioration of the entire sensitivity. Alternatively, there is a limit of the circuit performance.

The above configuration is further described with reference to FIGS. 1A, 1B, and 1C. When a change in the electrostatic capacitance is subjected to parallel plane approximation, a frequency characteristic 1 of an output current I of the capacitive electromechanical transducer to an input sound pressure (pressure of an input elastic wave) (refer to FIG. 1A) is formulated by the following Expression (1).

$$I=P/[(Zm+Zr)/(\varepsilon A^*V_b/d^2+j\omega C] \quad (1)$$

where e is a dielectric constant of vacuum, A is an area of an electrode (refer to an upper electrode 7 described later) of the electromechanical transducer, $V_b$ is a bias voltage applied between electrodes, d is a vacuum equivalent distance between the electrodes, P is the input sound pressure, Zm is a mechanical impedance of the vibrating membrane (refer to a vibrating membrane 8 described later), Zr is an acoustic impedance of a medium around the electromechanical transducer, and ω is an angular frequency of the input sound pressure, and C is an entire electrostatic capacitance. In this expression, because the entire electrostatic capacitance is relatively small, it can be said that the frequency function is the mechanical impedance Zm of the vibrating membrane.

Figure 1A:
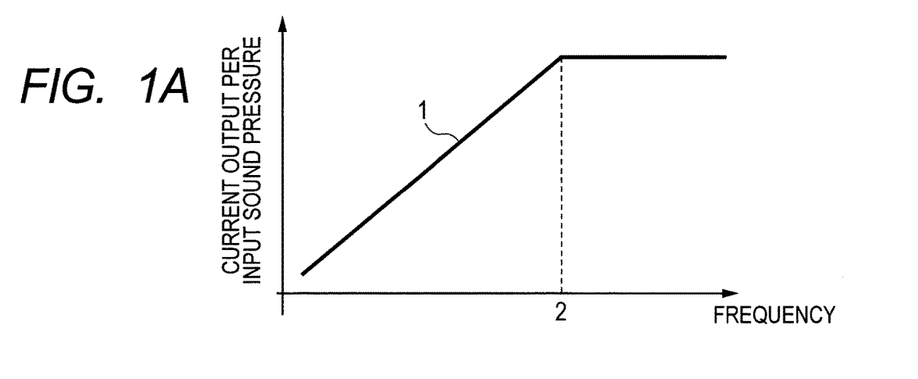
FIGS. 1A, 1B, and 1C are graphs showing the respective frequency characteristics of a capacitive electromechanical transducer provided disposed at a prestage of an ultrasonic detection device according to the present invention, an electric circuit disposed at a later stage thereof, and an entire device thereof.
Figure 1B:
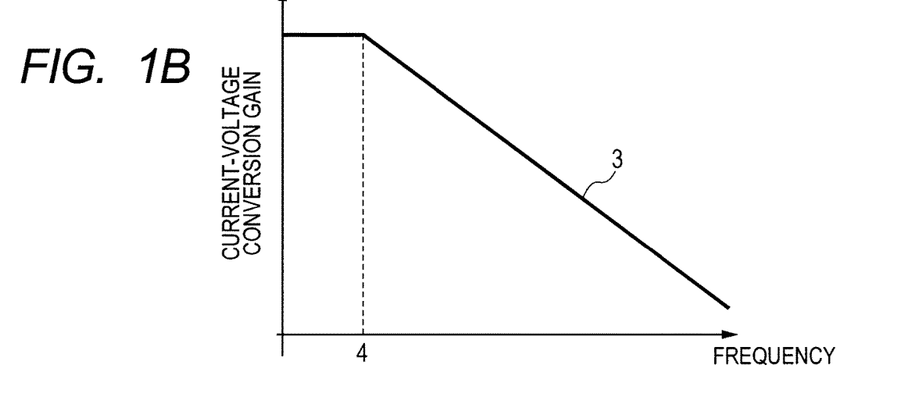

Zm is represented by the following Expression (2).

$$Zm=j^*km^*\{(\omega/\omega_0^2)-1/\omega\} \quad (2)$$

where km is the spring constant of the vibrating membrane, and the vibrating membrane is displaced in proportion to a pressure P in a domain of the frequency lower than the resonance angular frequency $\omega_0$ (which is close to the first cutoff frequency 2; refer to FIG. 1A). Zm approaches 0 in inverse proportion to the frequency in a range of from the low frequency domain to the resonance frequency. From this fact, in the frequency domain smaller than the resonance frequency of the vibrating membrane, the output current frequency characteristic 1 becomes a primary characteristic of the frequency. The curves of the frequency characteristics in FIGS. 1A to 1C are simplified and visually facilitated for description of the principle. In fact, for example, the shape is a little more deformed and gently changed in the vicinity of a shoulder portion, and the cutoff frequency is not always placed at a corner of the shoulder portion as shown in the graphs. The axis of abscissa of FIG. 1A represents a logarithmically expressed frequency, and the above-mentioned primary characteristic means a primary characteristic with respect to the logarithmically expressed frequency. Likewise, the above-mentioned inverse proportion means the inverse proportion to the logarithmically expressed frequency.

Further, as understood from the above Expression (1), the output current frequency characteristic 1 depends on not only the mechanical impedance Zm of the vibrating membrane, but also the acoustic impedance Zr constant in the use environment. Normally, the capacitive electromechanical transducer is frequently immersed in the liquid in use. The acoustic impedance of liquid is larger than the mechanical impedance of the vibrating membrane. In this case, the acoustic impedance of liquid is dominative in the frequency characteristic 1. As described above, the frequency at which the mechanical impedance Zm of the vibrating membrane is 0 is the resonance frequency of the vibrating membrane. In this case, the output current frequency characteristic 1 is a maximum value. The mechanical impedance of the vibrating membrane is originally the antiresonant frequency of the vibrating membrane, and becomes infinite. However, when the capacitive electromechanical transducer is used in the vicinity of a domain lower than the resonance frequency, because the antiresonant frequency is irrelevant, the domain in the vicinity of the antiresonant frequency is omitted in the output current frequency characteristic 1 of FIG. 1A. Considering the above-mentioned matters comprehensively, the output current frequency characteristic 1 represented by the above-mentioned Expression (1) is shown in FIG. 1A.

On the other hand, a frequency characteristic 3 of the current-voltage conversion and amplification circuit (refer to FIG. 1B) is formulated in the following Expression (3), and a second cutoff frequency 4 is represented by the following Expression (4).

$$G=Rf/(1+j\omega Rf^*Cf) \quad (3)$$

$$f=1/(2\pi Rf^*Cf) \quad (4)$$

where G is a gain of the electric circuit, Rf is the feedback resistance, Cf is the feedback capacitance, and f and ω are the frequency and the angular frequency of the input current. The electric circuit used in the configuration of the present invention is desired to be configured by an electric circuit having the primary characteristic with respect to the frequency as represented by Expression (3) (characteristic related to the logarithmically expressed frequency as with the above-mentioned frequency characteristic 1), and is not preferred to be configured by a circuit having a high-order characteristic.

In the present invention, the frequency characteristic 1 of the output current of the capacitive electromechanical transducer and the frequency characteristic 3 of the output of the electric circuit are combined together to realize the ultrasonic detection device having a lower frequency band than that of the conventional ultrasonic probe as a band. In the combination, in order to realize the ultrasonic detection device having an intended characteristic 5 (refer to FIG. 1C), a second cutoff frequency 4 of the frequency characteristic 3 of the output of the electric circuit is made smaller than the first cutoff frequency 2 of the frequency characteristic 1 of the output current of the capacitive electromechanical transducer. The reason is described above.

In this way, the output current frequency characteristic 1 of the capacitive electromechanical transducer is combined with the frequency characteristic 3 of the current-voltage conversion and amplification circuit to provide an output frequency characteristic 5 of the ultrasonic detection device. As shown in FIG. 1C, the effective frequency band is between a low band side cutoff frequency 101 and a high band side cutoff frequency 102. In this case, the low band side cutoff frequency 101 and the high band side cutoff frequency 102 are not always conformed to the second cutoff frequency 4 and the first cutoff frequency 3, respectively. This is because when the first cutoff frequency 3 and the second cutoff frequency 4 are close to each other, it is difficult that the output frequency characteristic 5 of the ultrasonic detection device becomes substantially flat in distribution between the low band side cutoff frequency 101 and the high band side cutoff frequency 102. The frequency characteristic 1 and the frequency characteristic 3 may be designed to provide a substantially flat distribution while keeping a given magnitude between the low band side cutoff frequency 101 and the high band side cutoff frequency 102.

In order to achieve this, for example, it is preferred that the slope of an inclined portion of the frequency characteristic 1 and the slope of an inclined portion of the frequency characteristic 3 be opposite in sign to each other and equal in absolute value to each other as much as possible. Further, it is preferred that the gain of the frequency characteristic 3 be increased.

Figure 1C:
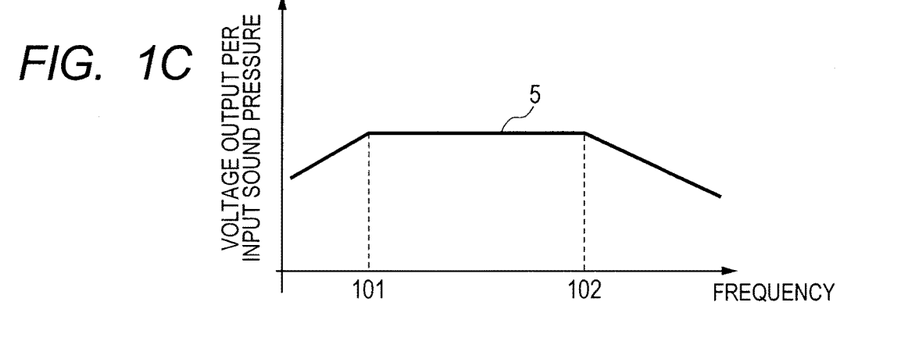

From the above viewpoint, it is preferred that, in the ultrasonic detection device having the broad band and the high sensitivity, for example, a frequency that is the geometric mean of the cutoff frequency 2 and the cutoff frequency 4 be in a range of from 0.4 MHz to 1.0 MHz, and have the frequency characteristic 5 shown in FIG. 1C. In the case where a value obtained by dividing the flat frequency band of the frequency characteristic 5 by its center value is 130%, when the geometric mean of the cutoff frequency 2 and the cutoff frequency 4 is set to 0.4 MHz, an ultrasonic wave of 0.2 MHz can be detected. Likewise, when the geometric mean of the cutoff frequency 2 and the cutoff frequency 4 is set to 1.0 MHz, an ultrasonic wave of 2.0 MHz can be detected.

Figure 6A:
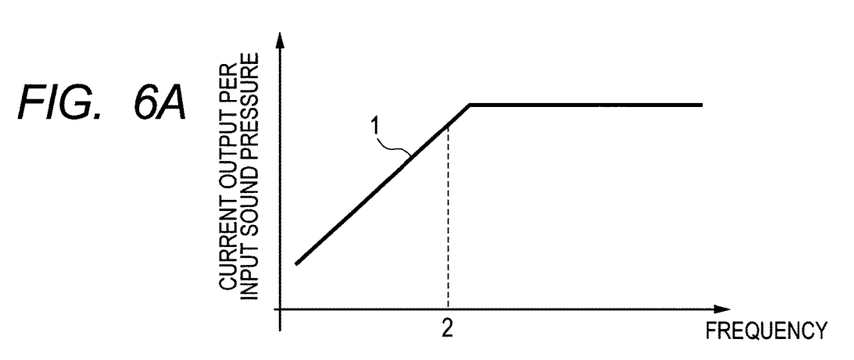
FIGS. 6A, 6B, and 6C are graphs showing frequency characteristics of a related art.
Figure 6B:
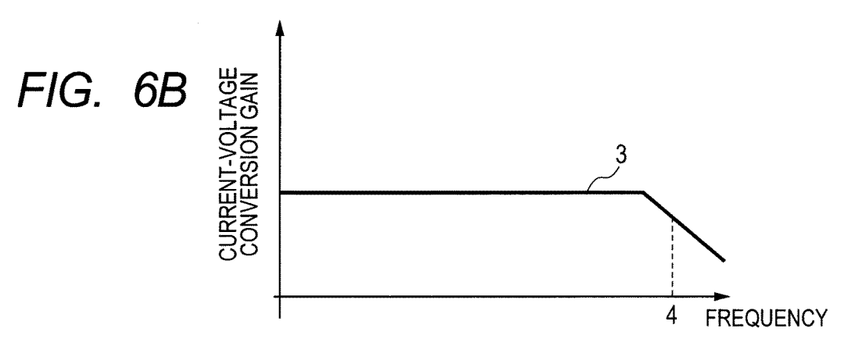
Figure 6C:
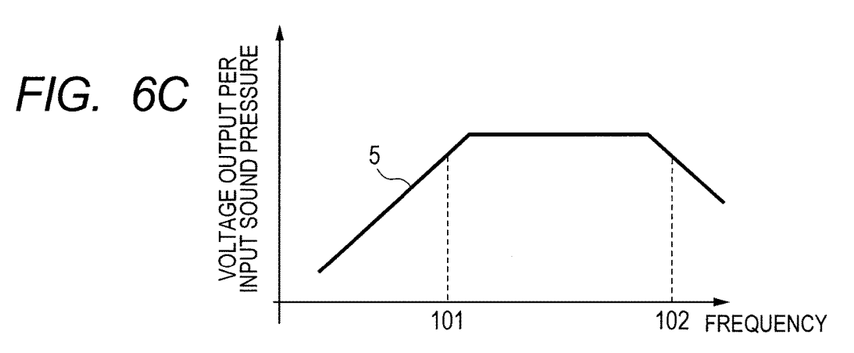

Up to now, when normal semiconductor or micromachining related material is used, in a liquid through which an ultrasonic wave from a living boy easily penetrates, the frequency characteristic of the capacitive electromechanical transducer is saturated and stable at about 3 MHz or higher. However, as described above, it is difficult to obtain the CMUT having the center in the vicinity of 1 MHz, and the high sensitivity. According to the present invention using the above-mentioned principle, such difficulty can be also eliminated. For comparison, the frequency characteristic of the conventional capacitive electromechanical transducer, the frequency characteristic of the conventional electric circuit, and the frequency characteristic of the conventional ultrasonic detection device are shown in FIGS. 6A, 6B, and 6C. The frequency characteristic of FIG. 6A is not substantially different from the frequency characteristic of FIG. 1A. However, in the frequency characteristic of FIG. 6B, the cutoff frequency 4 is at the high frequency side, and the gain is low totally as compared with the frequency characteristic of FIG. 1B. As a result, in the frequency characteristic of FIG. 6C, the low band side cutoff frequency 101 and the high band side cutoff frequency 102 range at the high frequency side, for example, 3 MHz to 10 MHz.

Hereinafter, embodiments having the configurations of the capacitive electromechanical transducer and the current-voltage conversion and amplification circuit embodied based on the above-mentioned principle are described with reference to the drawings.

Embodiment 1

Figure 2:
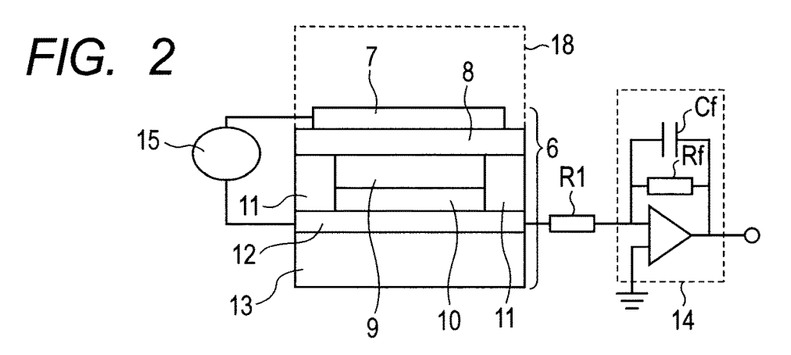
FIG. 2 is a diagram illustrating a configuration of an ultrasonic detection device according to an embodiment of the present invention.

An ultrasonic detection device according to Embodiment 1 is described. The configurations of a capacitive electromechanical transducer 6 (hereinafter, also called "cell") and an electric circuit 14 according to this embodiment are illustrated in FIG. 2. The capacitive electromechanical transducer 6 indicated as one cell includes an upper electrode 7, a vibrating membrane 8, a cavity 9, an insulating layer 10, support parts 11 that support the vibrating membrane 8, a lower electrode 12, and a substrate 13 that supports those members. The electric circuit 14 includes a resistor R1 connected to the upper electrode 7 and the lower electrode 12, and an operational amplifier having a feedback resistor Rf and a feedback capacitor Cf. The transducer 6 and the electric circuit 14 are configured to have the above-mentioned frequency characteristic.

FIG. 2 is an example of the configurations. When the vibrating membrane 8 is made of an insulator, the insulating layer 10 may or may not be provided. In this case, the vibrating membrane 8 and the support parts 11 may be made of the same material. The insulating layer 10 and the support parts 11 may be made of the same material. Structurally, the upper electrode 7 and the vibrating membrane 8 are bonded to each other, and vibrate integrally. From the viewpoint of improving the sensitivity, it is desired that the cavity 9 be maintained at a pressure lower than the atmospheric pressure. When the substrate 13 is formed of a conductive substrate such as a semiconductor substrate made of silicon, the substrate 13 and the lower electrode 12 may be integrated together. The output current frequency characteristic 1 depends on the mechanical impedance of the vibrating membrane 8 and the acoustic impedance of the use environment. Normally, the capacitive electromechanical transducer is frequently immersed in liquid 18 in use. The acoustic impedance of the liquid 18 is larger than the mechanical impedance of the vibrating membrane 8. Specifically, the liquid is water, an ultrasonic diagnosis grease, or an oil such as ricinus oil.

In general, the upper electrode 7 and the lower electrode 12 are desired to be made of metal, but may be made of low-resistant semiconductor. For example, the upper electrode 7 which is a second electrode can be made of at least one material of electric conductor selected from Al, Cr, Ti, Au, Pt, Cu, Ag, W, Mo, Ta, and Ni, semiconductor such as Si, and alloy selected from AlSi, AlCu, AlTi, MoW, AlCr, TiN, and AlSiCu. Further, the upper electrode 7 is disposed on at least one portion of an upper surface, a rear surface, and an interior of the vibrating membrane 8. Alternatively, the vibrating membrane 8 can be structured to serve also as the upper electrode 7 when the vibrating membrane 8 is made of electric conductor or semiconductor. The lower electrode 12 which is a first electrode can be made of the same electric conductor or semiconductor as that of the upper electrode 7. The electrode materials of the lower electrode 12 and the upper electrode 7 may be different from each other.

The dimensions of the respective parts in this embodiment are exemplified as follows. For example, a height of the cavity 9 is about 100 nm, but may be in a range of from 10 nm to 500 nm. A length of one piece of the cavity 9 is, for example, in a range of from 10 μm to 200 μm. The vibrating membrane 8 is made of, for example, SiN, but may be made of other insulating materials. The cavity 9 is held in a pressure reduction state with respect to the atmospheric pressure, and the vibrating membrane 8 is slightly recessed. The vibrating membrane and the electrodes are, for example, square, but may be circular or polygonal. The shape of the cavity 9 of the cell is also, for example, square, but may be other shapes.

During receiving operation, a DC voltage V is applied by a voltage source 15 in order to develop a potential difference between the upper electrode 7 and the lower electrode 12 of the cell 6 of the ultrasonic detection device. In receiving an ultrasonic wave, the vibrating membrane 8 oscillates, and a current is caused to flow by the amount as large as a change in the capacitance caused by the vibration. The current is amplified by the current-voltage conversion and amplification circuit 14.

Embodiment 2

Figure 3A:
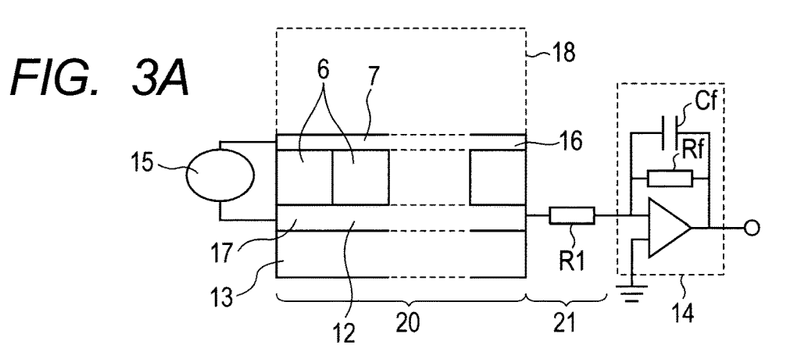
FIGS. 3A and 3B are configuration diagrams of an ultrasonic detection device according to another embodiment of the present invention.
Figure 3B:
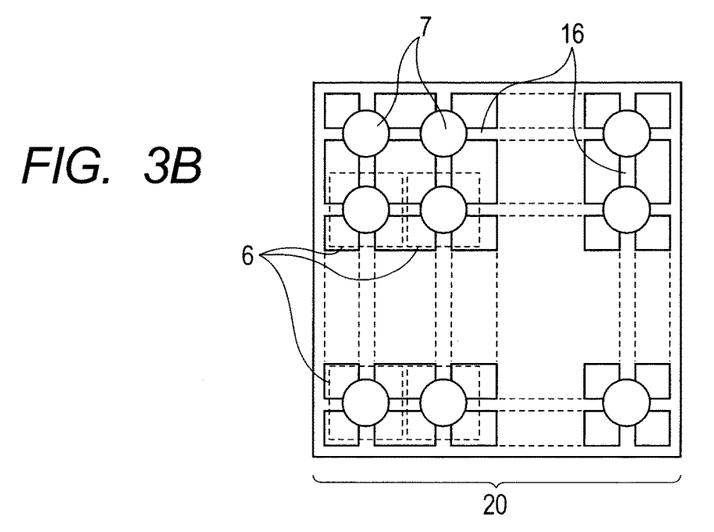

An ultrasonic detection device according to Embodiment 2 is described. The configuration of this embodiment is illustrated in FIGS. 3A and 3B. FIG. 3A illustrates a conceptual cross-sectional view of the ultrasonic detection device, and FIG. 3B illustrates a plan view of an element 20. Portions indicated by broken lines in FIGS. 3A and 3B represent that drawing of the structure is omitted except for a perspective portion of the cell 6. In this embodiment, the multiple cells 6 are arranged on the substrate 13. The structures of each cell 6 and the electric circuit 14 are the same as those described in Embodiment 1. The upper electrodes 7 and the lower electrodes 12 of the multiple cells 6 are electrically connected by electrode coupling wiring parts 16 and 17, respectively, so that the multiple cells 6 are rendered conductive to each other. As illustrated in FIG. 3B, the cells 6 are arranged two-dimensionally at regular intervals to form one element 20. The device is used, for example, under a state in which the upper electrodes 7 of the element 20 are brought into contact with the liquid 18 excellent in propagation of the ultrasonic wave. From the viewpoint of the detection sensitivity and the facility of signal processing, it is desired that the mechanical characteristics of the vibrating membranes 8 and the depths of the cavities 9 be uniform in the multiple cells 6. Within the element 20, the arrangement of the cells 6 is in a square lattice in the illustrated example, but may be in a zigzag shape or a hexagonal close-packed shape. The arrangement form and the number of cells 6 within the element 20 can be appropriately determined as occasion demands. In the illustrated example, the shape of the vibrating membranes 8 is circular, but may be polygonal. In this way, in this embodiment, the capacitors each made up of the lower electrode 12 (first electrode) and the upper electrode 7 (second electrode) include the multiple spaces 9 and the multiple second electrodes or vibrating membranes 8. The frequency characteristic of the output current of the element 20 is determined according to factors including the average of the mechanical characteristics of the multiple second electrodes or vibrating membranes 8, and the electrostatic capacitance of the capacitor.

In this embodiment, the domain where the multiple upper electrodes 7 are rendered conductive to each other forms an ultrasonic detection domain, and increases the sensitivity as compared with that of Embodiment 1 including one cell. In this embodiment, it may be said that the element 20 including the multiple cells configures one capacitive electromechanical transducer. In this case, the frequency characteristic 1 of the capacitive electromechanical transducer (refer to FIG. 1A) is determined, as described above, according to the average value of the mechanical characteristics of the multiple vibrating membranes 8. Further, the magnitude of the current output of the element 20 is substantially proportional to the total area of the upper electrodes 7 on the multiple vibrating membranes 8. Other configurations are identical with those in Embodiment 1.

Embodiment 3

Figure 4A:
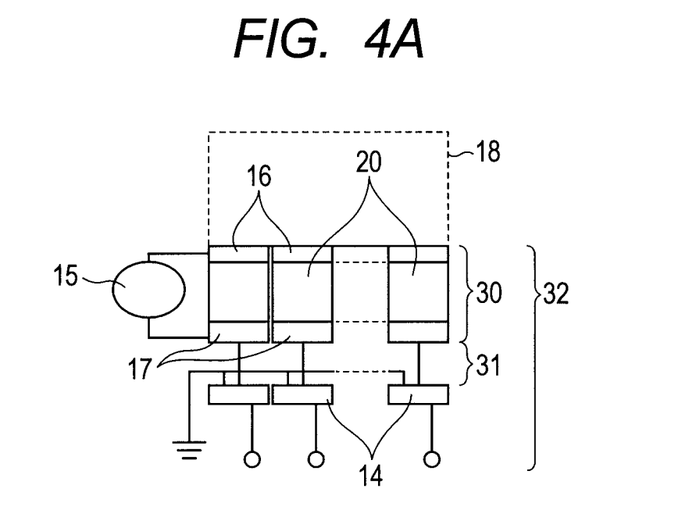
FIGS. 4A and 4B are configuration diagrams of an ultrasonic detection device according to still another embodiment of the present invention.
Figure 4B:
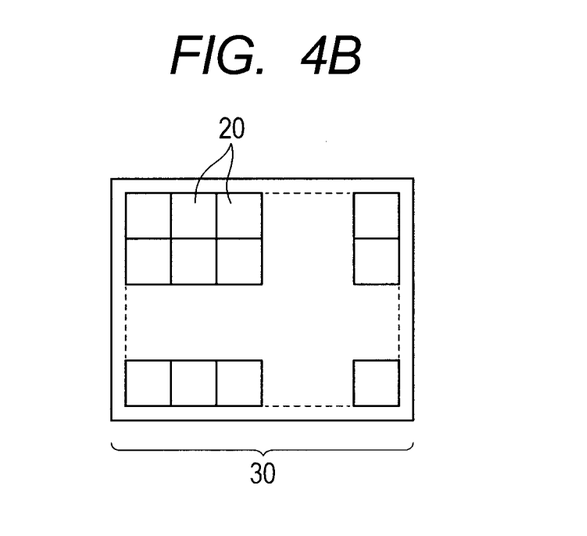

An ultrasonic detection device according to Embodiment 3 is described. The configuration of this embodiment is illustrated in FIGS. 4A and 4B. FIG. 4A which is a top view is a conceptual cross-sectional view illustrating the entire configuration of an ultrasonic detection device 32, and also illustrates electric coupling including wirings 31 and current-voltage conversion and amplification circuits 14. FIG. 4B is a plan view of the ultrasonic detection device 32. In FIG. 4B, the wirings 31 and the current-voltage conversion and amplification circuits 14 are hidden below. However, those members may be arranged laterally. Similarly, in FIGS. 4A and 4B, portions indicated by broken lines show that drawing of the structure is omitted. An ultrasonic detection device 30 according to this embodiment is configured so that the elements 20 of Embodiment 2 are arranged two-dimensionally. Any one of the upper electrodes 7 connected by the wiring parts 16 and lower electrodes 12 connected by the wiring parts 17 are electrically separated in each of the elements 20. Similarly, in this embodiment, the upper electrodes 16 are brought into contact with the liquid 18 excellent in propagation of the ultrasonic wave. An output of each element 20 is transmitted to each current-voltage conversion and amplification circuit 14 by each wiring 31 to conduct voltage conversion. As a result, the ultrasonic signal can be detected as a two-dimensional distribution. Similarly, in this example, the frequency characteristic 1 of each element 20 is determined according to the average value of the mechanical characteristics of the multiple vibrating membranes 8. Further, the amplitude of the current output of each element 20 is substantially proportional to the total area of the multiple upper electrodes 7. In the ultrasonic detection device according to this embodiment, and the capacitors are arranged two-dimensionally, and the vibrating information of the second electrodes or the vibrating membranes 8 can be detected two-dimensionally. Other configurations are identical with those in Embodiment 1.

Incidentally, the configuration of the above-mentioned embodiment can be used as a device that generates a sound wave. A voltage obtained by superimposing a minute AC voltage on the DC voltage is applied between the upper electrodes 7 (or the upper electrode coupling wiring parts 16) and the lower electrodes 12 (or the lower electrode coupling wiring parts 17) by the voltage source 15 to forcedly vibrate the vibrating membranes 8 for generation of the sound wave. In this case, the frequency characteristic mainly has the same transmission characteristic as that of the output current frequency characteristic 1 of the capacitive electromechanical transducer. The sound wave generation device arranges the vibrating membranes 8 two-dimensionally as in the above-mentioned Embodiment 2 or Embodiment 3 to generate a larger sound wave. Further, when the generation area is increased, the directionality of the sound wave can be increased, and the diffraction can be decreased.

Embodiment 4

Figure 5:
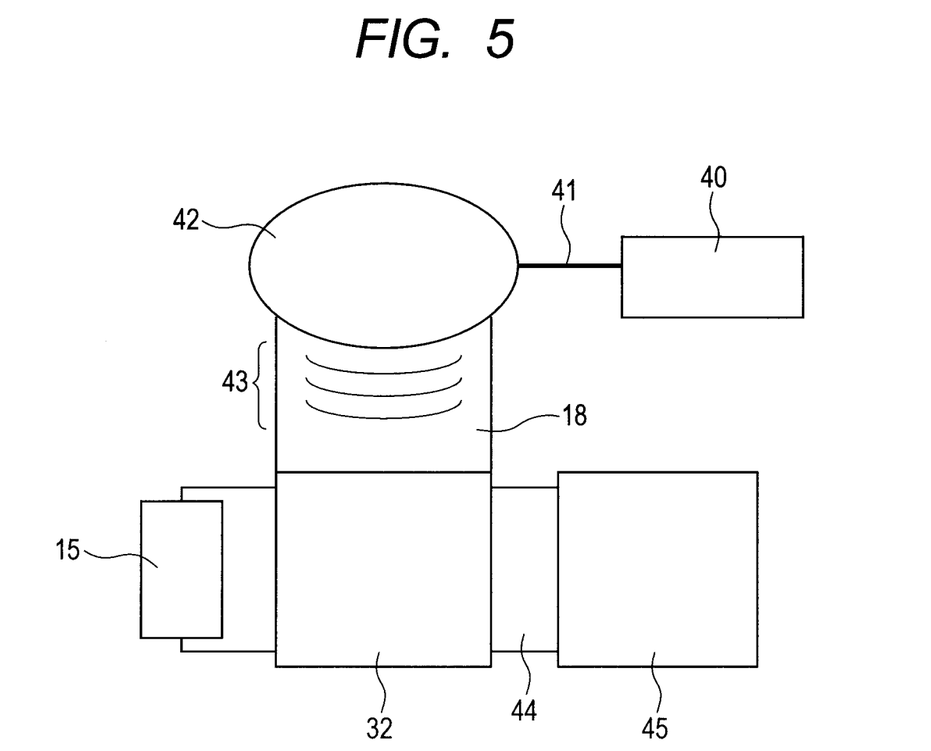
FIG. 5 is a configuration diagram of an ultrasonic diagnostic device according to an embodiment of the present invention.

An ultrasonic diagnostic device according to Embodiment 4 is described. The configuration of this embodiment is illustrated in FIG. 5. Light 41 emitted from a light source 40 is propagated and applied to a body tissue 42, to thereby generate an ultrasonic wave 43 which is called "photoacoustic wave". That is, the light is absorbed by a portion large in light absorption coefficient that exists within the body tissue, and that portion is heated. Then, the heated portion is expanded, and an elastic wave is generated by expansion. The ultrasonic wave 43 is, for example, about 200 kHz to 2 MHz as described above although being different according to material or individual configuring the body tissue. The ultrasonic wave (photoacoustic wave) 43 passes through the liquid 18 excellent in propagation of the ultrasonic wave, and is detected by the ultrasonic detection device 32. The current-voltage converted and amplified signal is transmitted to a signal processing system 45 through a signal bus 44. A signal of the detection result is processed by the signal processing system 45 to extract the body information. When the ultrasonic detection device 32 is configured as in the above-mentioned Embodiment 3, the two-dimensional ultrasonic distribution can be detected, and a wide-range distribution can be captured by scanning the ultrasonic detection device 32. Because the ultrasonic wave has a sound speed, a time difference of arrival waves (time waveform) may be analyzed to obtain time information, and information in the depth direction can be acquired. In this case, a reconstruction function can be provided to the signal processing system 45 so as to extract the three-dimensional body information. Further, the received signal may be subjected to Fourier transform to obtain the frequency characteristic so as to acquire an image or the like.

As described above, a technique by which a cross-sectional image or a three-dimensional image of a specimen (object to be tested) is acquired by using the photoacoustic effect has been generally known as a photoacoustic tomography, and called "PAT technology" from its initial.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-254752, filed Nov. 6, 2009, which is hereby incorporated by reference herein in its entirety.

The invention claimed is:

1. An ultrasonic detection device comprising:
a capacitive electromechanical transducer for receiving an ultrasonic wave including at least one cell that includes a first electrode and a second electrode disposed opposite from the first electrode, a space being between the first electrode and the second electrode; and
an electric circuit for converting a current, which is output from the capacitive electromechanical transducer, into a voltage,
wherein frequency characteristic of output current of the capacitive electromechanical transducer with respect to an ultrasonic wave to be received has a first slope domain where a value becomes small as a frequency becomes low and a first flat domain;
wherein frequency characteristic of output voltage of the electric circuit with respect to a current to be input has a second slope domain where a value becomes small as the frequency becomes high and a second flat domain;
wherein the ultrasonic detection device has a range where the first slope domain overlaps with the second slope domain; and
wherein the frequency band of the first flat domain is higher than the frequency band of the first slope domain, and the frequency band of the second flat domain is lower than the frequency band of the second slope domain.

2. The ultrasonic detection device according to claim 1, wherein the at least one cell further includes a vibrating membrane that vibratably supports the second electrode.

3. The ultrasonic detection device according to claim 2, wherein the first slope domain is in a domain lower than a resonance frequency of the vibrating membrane.

4. The ultrasonic detection device according to claim 1, wherein the first slope domain is in a domain lower than a frequency showing a maximum value of the output current of the capacitive electromechanical transducer with respect to the ultrasonic wave to be received.

5. The ultrasonic detection device according to claim 1, wherein the first slope domain is in a domain lower than a frequency showing a value lowered by 3 dB at a frequency side lower than a frequency at which the output current of the capacitive electromechanical transducer shows a maximum value with respect to the ultrasonic wave to be received.

6. The ultrasonic detection device according to claim 1, wherein the second slope domain is in a domain higher than a frequency showing a maximum value of the output voltage of the electric circuit with respect to the current to be input.

7. The ultrasonic detection device according to claim 1, wherein the second slope domain is in a domain higher than a frequency showing that the output voltage of the electric circuit is lowered by 3 dB than a low band with respect to the current to be input.

8. The ultrasonic detection device according to claim 1, wherein the capacitive electromechanical transducer includes a plurality of cells, where some of cells constitutes an element, and
wherein the frequency characteristic of output current of the capacitive electromechanical transducer with respect to the ultrasonic wave to be received is determined according to factors including an average of mechanical characteristic of a plurality of second electrodes disposed in the plurality of cells and electrostatic capacitances of the element.

9. The ultrasonic detection device according to claim 1, wherein the frequency characteristic of the output current of the capacitive electromechanical transducer with respect to the ultrasonic wave to be received is frequency characteristic of the output current of the capacitive electromechanical transducer with respect to a unit sound pressure of an ultrasonic wave to be received.

10. The ultrasonic detection device according to claim 1, wherein the frequency characteristic of the output voltage of the electric circuit with respect to the current to be input is frequency characteristic of a conversion gain of the output voltage of the electric circuit with respect to the current to be input.

11. The ultrasonic detection device according to claim 1, wherein the capacitive electromechanical transducer includes a plurality of cells, where some of cells constitutes an element.

12. The ultrasonic detection device according to claim 11, wherein the plurality of elements is disposed on a substrate.

13. The ultrasonic detection device according to claim 1, wherein the capacitive electromechanical transducer receives an ultrasonic wave generated in an object to be tested by absorption of light.

14. The ultrasonic detection device according to claim 1, wherein the capacitive electromechanical transducer transmits an ultrasonic wave.

15. An ultrasonic diagnostic device comprising:
a light source;
an ultrasonic detection device for detecting an ultrasonic wave generated by applying light emitted from the light source to an object to be tested; and
a signal processing system that processes a signal output from the ultrasonic detection device,
wherein the ultrasonic detection device comprises:
a capacitive electromechanical transducer for receiving an ultrasonic wave including at least one cell that includes a first electrode and a second electrode disposed opposite from the first electrode, a space being between the first electrode and the second electrode; and
an electric circuit for converting a current, which is output from the capacitive electromechanical transducer, into a voltage, wherein frequency characteristic of output current of the capacitive electromechanical transducer with respect to an ultrasonic wave to be received has a first slope domain where a value becomes small as a frequency becomes low and a first flat domain;

wherein frequency characteristic of output voltage of the electric circuit with respect to a current to be input has a second slope domain where a value becomes small as the frequency becomes high and a second flat domain;

wherein the ultrasonic detection device has a range where the first slope domain overlaps with the second slope domain; and wherein the frequency band of the first flat domain is higher than the frequency band of the first slope domain, and the frequency band of the second flat domain is lower than the frequency band of the second slope domain.

16. An ultrasonic detection device comprising:
a capacitive electromechanical transducer for receiving an ultrasonic wave including at least one cell that includes a first electrode and a second electrode disposed opposite from the first electrode, a space being between the first electrode and the second electrode; and
an electric circuit for converting a current, which is output from the capacitive electromechanical transducer, into a voltage,
wherein frequency characteristic of output current of the capacitive electromechanical transducer with respect to an ultrasonic wave to be received has a first flat domain where a value is constant for frequency and a first slope domain where a value becomes small as a frequency becomes low;
wherein frequency characteristic of output voltage of the electric circuit with respect to a current to be input has a second flat domain where a value is constant for frequency and a second slope domain where a value becomes small as the frequency becomes high;
wherein the ultrasonic detection device has a portion where the first slope domain overlaps with the second slope domain; and
wherein the frequency band of the first flat domain is higher than the frequency band of the first slope domain, and the frequency band of the second flat domain is lower than the frequency band of the second slope domain.

17. The ultrasonic detection device according to claim 16, wherein the at least one cell further includes a vibrating membrane that vibratably supports the second electrode.

18. The ultrasonic detection device according to claim 17, wherein the frequency in a frequency domain of the first slope domain is lower than a first frequency, and
wherein the first frequency is a resonance frequency of the vibrating membrane.

19. The ultrasonic detection device according to claim 16, wherein the frequency in a frequency domain of the first slope domain is lower than a first frequency, and
wherein the first frequency is a frequency showing a maximum value of the output current of the capacitive electromechanical transducer with respect to the ultrasonic wave to be received.

20. The ultrasonic detection device according to claim 16, wherein the frequency in a frequency domain of the first slope domain is lower than a first frequency, and
wherein the first frequency is a frequency showing a value lowered by 3 dB at a frequency side lower than a frequency at which the output current of the capacitive electromechanical transducer shows a maximum value with respect to the ultrasonic wave to be received.

21. The ultrasonic detection device according to claim 16, wherein the frequency in a frequency domain of the second slope domain is higher than a second frequency, and
wherein the second frequency is a frequency showing a maximum value of the output voltage of the electric circuit with respect to the current to be input.

22. The ultrasonic detection device according to claim 16, wherein the frequency in a frequency domain of the second slope domain is higher than a second frequency, and
wherein the second frequency is a frequency showing that the output voltage of the electric circuit is lowered by 3 dB than a low band with respect to the current to be input.

23. The ultrasonic detection device according to claim 16, wherein the frequency characteristic of the output current of the capacitive electromechanical transducer with respect to the ultrasonic wave to be received is frequency characteristic of the output current of the capacitive electromechanical transducer with respect to a unit sound pressure of the ultrasonic wave to be received.

24. The ultrasonic detection device according to claim 16, wherein the frequency characteristic of the output voltage of the electric circuit with respect to the current to be input is frequency characteristic of a conversion gain of the output voltage of the electric circuit with respect to the current to be input.

25. An ultrasonic diagnostic device comprising:
a light source;
an ultrasonic detection device for detecting an ultrasonic wave generated by applying light emitted from the light source to an object to be tested; and
a signal processing system that processes a signal output from the ultrasonic detection device,
wherein the ultrasonic detection device comprises:
a capacitive electromechanical transducer for receiving an ultrasonic wave including at least one cell that includes a first electrode and a second electrode disposed opposite from the first electrode, a space being between the first electrode and the second electrode; and
an electric circuit for converting a current, which is output from the capacitive electromechanical transducer, into a voltage,
wherein frequency characteristic of output current of the capacitive electromechanical transducer with respect to an ultrasonic wave to be received has a first flat domain where a value is constant for frequency and a first slope domain wherein a value becomes small as a frequency becomes low;
wherein frequency characteristic of output voltage of the electric circuit with respect to a current to be input has a second flat domain where a value is constant for frequency and a second slope domain where a value becomes small as the frequency becomes high;
wherein the ultrasonic detection device has a range where the first slope domain overlaps with the second slope domain; and
wherein the frequency band of the first flat domain is higher than the frequency band of the first slope domain, and the frequency band of the second flat domain is lower than the frequency band of the second slope domain.

* * * * *